United States Patent
Arumughan et al.

(10) Patent No.: US 7,632,530 B2
(45) Date of Patent: Dec. 15, 2009

(54) PROCESS FOR THE PREPARATION OF HIGH PURITY PHYTOSTEROLS

(75) Inventors: Chami Arumughan, Trivandrum (IN); Das Retna Sobankumar, Trivandrum (IN); Andikkannu Sudaresan, Trivandrum (IN); Sreeja Sadasivan Nair, Trivandrum (IN); Kannan Yohesh, Trivandrum (IN); Leelavathy Rajam, Trivandrum (IN)

(73) Assignee: Council of Scientific and Industrial Research, New Delhi (IN)

( * ) Notice: Subject to any disclaimer, the term of this patent is extended or adjusted under 35 U.S.C. 154(b) by 797 days.

(21) Appl. No.: 11/373,933

(22) Filed: Mar. 13, 2006

(65) Prior Publication Data

US 2007/0142652 A1 Jun. 21, 2007

(30) Foreign Application Priority Data

Nov. 8, 2005 (IN) .................. 2987/DEL/2005

(51) Int. Cl.
*C07J 9/00* (2006.01)
(52) U.S. Cl. ...................... 426/494; 552/545
(58) Field of Classification Search ................ 426/494; 552/545
See application file for complete search history.

(56) References Cited

U.S. PATENT DOCUMENTS

| | | | | |
|---|---|---|---|---|
| 2,516,834 A | * | 8/1950 | Bohm | 552/545 |
| 2,704,764 A | * | 3/1955 | Mattikow et al. | 549/413 |
| 3,153,055 A | * | 10/1964 | Smith et al. | 549/413 |
| 4,044,031 A | * | 8/1977 | Johansson et al. | 552/545 |
| 4,222,949 A | * | 9/1980 | Foster | 552/555 |
| 4,614,620 A | * | 9/1986 | Konai et al. | 552/501 |
| 5,117,016 A | * | 5/1992 | Tackett et al. | 552/545 |
| 6,303,805 B1 | | 10/2001 | Lyu et al. | |
| 6,762,312 B1 | * | 7/2004 | Hattori et al. | 552/545 |
| 6,979,743 B1 | * | 12/2005 | Schwarzer et al. | 552/545 |
| 7,173,144 B1 | * | 2/2007 | Hattori et al. | 552/545 |
| 7,244,856 B2 | * | 7/2007 | Sicre et al. | 552/545 |
| 2005/0054621 A1 | * | 3/2005 | Gako-Golan et al. | 514/171 |
| 2005/0250953 A1 | * | 11/2005 | May et al. | 549/413 |
| 2006/0166951 A1 | * | 7/2006 | Sanbom | 514/169 |

FOREIGN PATENT DOCUMENTS

| EP | 0 329 347 A | 8/1989 |
|---|---|---|
| GB | 489623 | 7/1938 |
| GB | 895145 | 5/1962 |
| WO | WO 03/080778 | 10/2003 |

* cited by examiner

*Primary Examiner*—Anthony Weier
(74) *Attorney, Agent, or Firm*—Frommer Lawrence & Haug LLP; Thomas J. Kowalski; Russell A. Garman

(57) ABSTRACT

The present invention provides an isolation process of the pure sterols from the SODD by simple acid catalyzed esterification and the separation of the reagents by distillation and water washing followed by the crystallization of phytosterols and purification. Soybean oil deodorizer distillate (SODD) and distillate from other vegetable oil refining contain free sterols, in addition to steryl esters, tocopherols squalene and unknown compounds. The process is also applicable to other vegetable oil distillate containing more than 1% phytosterols in the free form. Phytosterols thus obtained is of high purity (95-99%) and high yield (80-90%) and contains β-sitosterol, Stigmasterol and campesterol.

8 Claims, 1 Drawing Sheet

PROCESS FOR THE PREPARATION OF HIGH PURITY PHYTOSTEROLS

This application claims priority benefits from Indian Patent Application No. 2987DEL2005 filed Nov. 8, 2005.

The present invention relates to a process for the preparation of phytosterols from deodourizer distillate from vegetable oils.

Phytosterols such as β-sitosterol, campesterol, stigmasterols have received scientific attention recently because of their health promotion as feedstock for pharmaceuticals. Phytosterols as health food supplement has attributed to their cholesterol lowering effect as evidenced by numerous scientific studies. Phytosterols are widely distributed among plants and plant products with oil seeds being very rich source. They occur as free sterols and esterified fatty acids and ferulic acids etc. Being fat-soluble phytosterols get extracted along with oil when oil seeds are processed for vegetable oil production with concentration ranging from 1.0 to 2.0%. During physical refining of edible oils, sufficient amount of these sterols get distilled along with free fatty acids and other minor constituents in the deodourizer and deacidification process. Thus the by-product namely deodourizer distillate (DOD) of vegetable oils, which is rich commercial source for phytosterols, tocopherols, squalene etc, is of secondary importance. Consequent to the demand for health food supplements recovery of phytosterols from DOD through commercially feasible process assumes importance. Currently products like margarines and shortenings fortified with phytosterols are marketed. Phytosterols have been shown to prevent reabsorption of cholesterol from the gut resulting lowering cholesterol.

In this new process, phytosterols with more than 97% purity was obtained from DOD by simple esterification and crystallization method, which is cost effective and commercially adaptable. After esterification excess of the methanol was separated by vacuum distillation and acid catalyst removed by water washing followed by crystallization and filtration that yielded free sterols as crystals. The impurities in the crystals could be removed using chilled hexane to obtain 97-99% pure sterol crystals.

The other products obtained are fatty acid methyl esters and residue left after crystal separation rich in tocopherols. The fatty acid methyl esters (95%) could be used for oleochemicals or for bio-diesel while the residue could be further processed to recover high purity tocopherols. The process presented here is an integrated approach to value addition to DOD through recovery of all the constituents of high purity that otherwise treated as low value product.

One of the prior patents [Eastman Kodak Co; Published at the patent office, 25 Southampton Building, London, WC2. Separation of sterols. Patent Number GB895145 (1962)] sterols separated after sopaonification, neutralization, and solvent extraction. In this method DOD was saponified with methanolic alkaline medium and acidulated the saponified mixture and separated glycerol-containing compounds by water washing and finally sterols extracted with a solvent mixture of methanol, acetone, methyl ethyl ketone, and water. The residue containing fatty acids therefore it is difficult to isolate other components like tocopherols, squalene etc. from the mother liquor. [Hobman Peter Graeme C O New Ze; Keen Alan Robert C O Neala; Ward David Douglas C New Zeala, New Zealand Dairy Res. Inst (NZ). Improvements in or relating to methods of removing sterols and/or other steroidal compounds from edible fats and/or oil from which such sterols and/or other steroidal Compounds have been removed. European Patent No. EP 03293 47 (1989)] in this study a solvent system was used to separate the sterols from fats and/or oils. The authors could reduces campesterols 313 ppm to 239 ppm removal is 23.6%, stigmasterols 303 ppm to 217 ppm removal is 28.4%, β-sitosterol 752 ppm to 627 ppm removal is 16.6% from the soy bean oil remaining sterols retained in the oil phase. This method is useful to reduce the steroidal compounds from the source not for the complete separation which contains lower range of steroidal compound. In yet another patent [Kodali Dharma R (US), Cargill INC (US), Removal of Sterols from fats and oils, U.S. Pat. No. 6,303,803 (2001)] Sterols were separated from the fats and oils by this method, extraction of sterols from fats and oils to lecithin water phase This method was indented towards for the reduction of sterols in the oils and fats and therefore not for the complete separation of the sterols from the oil and DOD. In another patent [Eastman Kodak Co; W P Thopson & Co, 12, Church Street, Liverpool, Charted patent Agents. Improvements in high vacuum distillation of materials containing sterols. Patent Number GB489623]. Sterols concentrated using short path high vacuum distillation and purified by solvent extraction and crystallization or removed the fatty matter by saponification and solvent extraction purity and yield not mentioned, this process was combination of High vacuum distillation and solvent extraction. In a recent patent [I.P. Holdings, L.L.C [US/US] 12700 west Dodge Road, Omaha, Nebr. 68154(US), Copeland, Dick [US/US] 12929 Seward street, Omaha, Nebr. 68154 (US) Belcher, Maurice. [US/US] 16124 Dewey Avenue, Omaha, Nebr. 68154[US] (2003)] Methods for treating Deodorizer distillate, International patent Number WO 03/080778 A2] sterols and tocopherols in Soybean oil DOD were concentrated for the further purification. In this process acetone was used to separate sterols and tocopherols from the residue. The purity of the sterols after the fatty acid distillation and acetone separation was only 76%. [From the above reports it could be reasonably assumed that an economic method suitable for separation of phytosterols from SODD is currently not available.

OBJECTIVES OF THE INVENTION

The main objective of the present invention is to provide a process for the preparation of high purity phytosterols from SODD and other vegetable oil DOD.

Yet another object is the reduction of number of process steps and a integrated approach to recovery of all the valuable components from vegetable oil DOD such as Phytosterols, tocopherols, fatty acid methyl esters.

Yet another object of the present innovation is to develop simple and economically more viable process for 99% purity phytosterols from SODD.

Yet another object is to develop process for recovery of phytosterols from other DOD from Sunflower oil, Rice bran oil, Palm oil etc.

Yet another object of the invention is recover fatty acid methyl esters by simple distillation for oleo chemical application or for bio-diesel.

Yet another object of the invention is to enrich a fraction with tocopherols for further processing to high purity natural Vitamin-E.

Still another object of the present invention is the recovery of the reagents used for the esterification for recycling so as to make the process ceo-friendly.

SUMMARY OF THE INVENTION

Accordingly the present invention provides a process for the preparation of high purity phytosterols from deodourizer distillate from vegetable oils which comprises mixing deodourizer distillate from vegetable oils with a methanolic solution of sulfuric acid in a ratio of 1:1 to 1:1.5 (v/v), stirring the above said reaction mixture, at a temperature of 50-85° C., for a period of 2-4 hrs, distilling of the excess of methanol from the above said reaction mixture under vacuum, adding brine solution to the above said reaction mixture to separate sulfuric acid and removing the lower layer to obtain the ester layer, washing the above said ester layer with hot water till all of the acid and salts are removed, followed by crystallization at a temperature in the range of 0-25° C. for a period of 1-10 hrs, filtering and washing the resultant crystals obtained with chilled n-hexane, at a temperature of 0-10° C. to obtain the desired high purity phytosterols.

In an embodiment of the present invention the vegetable oil used for obtaining deodourizer distillate is selected from the group consisting of soybean oil, sunflower oil, rice bran oil, palm kernel oil and coconut oil.

In yet another embodiment the sulfuric acid in methanolic solution of sulfuric acid used is in the range of 1-10%.

In yet another embodiment the crystallization of the sterols is facilitated by bound water retained after water washing or added externally.

In yet another embodiment the excess water present in the ester layer is released by controlled heating and is removed by decantation or centrifugation.

In yet another embodiment the yield of fatty acid methyl esters obtained is 60-70% of DOD with 95-99% purity.

In still another embodiment the yield of phytosterols obtained is in the range of 80-90% of free sterols available in DOD with 95-99% purity.

DETAIL DESCRIPTION OF THE INVENTION

Figure 1:
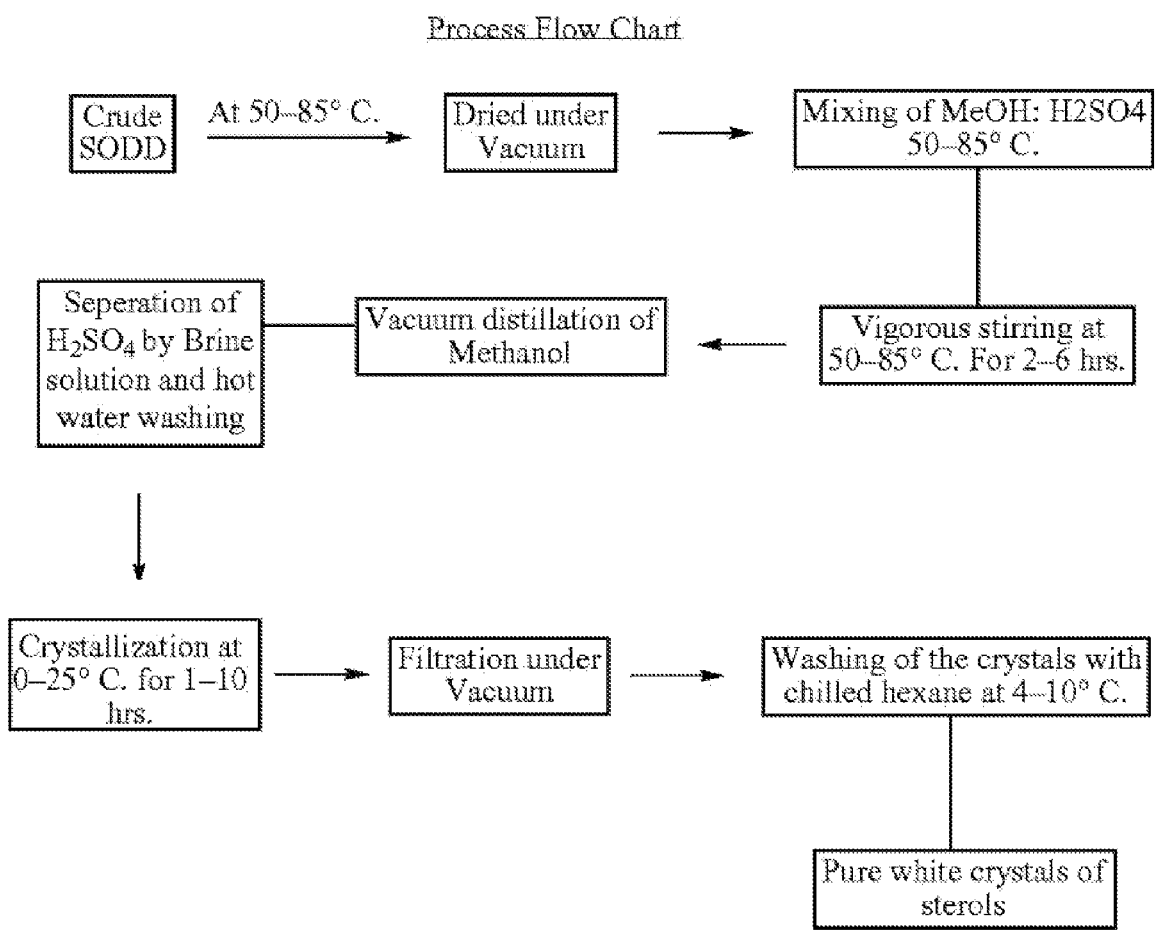
FIG. 1 shows the flowchart process of the instant invention.

The new process based on SODD is briefly as follows. Soya bean oil Deodorizer Distillate contains approximately 5 to 15% free sterols. Free sterols are mixture of β-sitosterol (35-45%), campesterol (15-25%), Stigmasterol (35-45%) and Avenasterol (2-8%). (Table 2) The distillate also contains about 2% moisture and other constituents (Table 1). And also it is rich source for tocopherols and tocotrienols (Table 3) The Distillate was first dried under vacuum to remove the moisture content and the residual moisture content was brought down to <0.5%. The distillate was mixed with equal volume of methanol sulphuric acid reagent and the mixture was heated for a period of 1-4 hrs under vigorous stirring to avoid layer separation. After the completion of esterification, 70-80% methanol remain as excess. The excess methanol was separated by vacuum distillation at 60-70° C. Hot brine solution was added to the esterified mass to facilitate the separation of acid catalyst and residual methanol. The lower layer contains brine solution and acid catalyst was drained off. The ester layer retained in the separating funnel was washed with hot distilled water till free of acid and salt. All the washing procedure conducted at 60-90° C. The esterified mass was collected in a flask and kept in a crystallizer provided with programmer to control the cooling rates. The esterified mixture was then cooled to between 0-25° C. and kept constantly for 1-15 hrs. The residual water presents in the esterified mass enhances the crystallization of the phytosterols from the esterified mixture. After the end of the cooling time the crystals were filtered under vacuum. Filtration is usually employed to separate the fractionally crystallized sterols from the mother liquor, although any of the other well-known methods of separating solids from liquids such as decanting, and centrifugation can also be utilized. After filtration chilled hexane 4-10° C. was passed through the crystal bed to purify sterol crystals. Finally the crystals were dried at ambient condition until free from residual solvent. The phytosterols crystals thus obtained were analyzed for yield and purity using TLC, HPLC, GC-MS, and NMR. (Table 4)

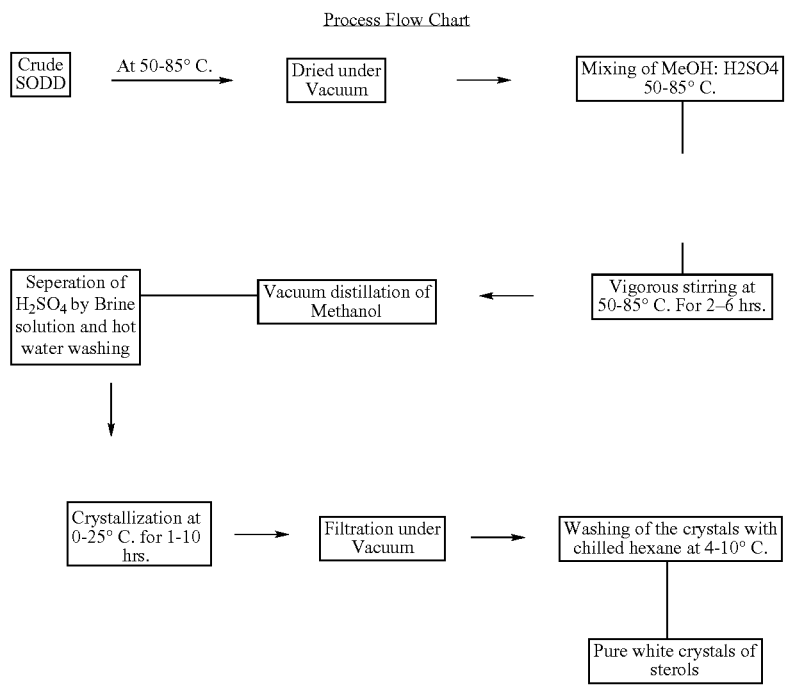

The following examples are given by the way of illustration and should not be construed to limit the scope of the invention.

Example 1

100 g of the SODD was dried under vacuum and mixed with equal volume of 98:2 methanolic sulphuric acid reagent and stirred vigorously for 2 Hrs. After the esterification excess of the methanol was distilled out under vacuum. To the mixture added 50 ml of brine solution at 60° C. and removed the lower layer. The mixture washed with 250 ml of hot distilled water until free from acid and salt. The esterified mixture was crystallized at 10° C. for 10 hrs in a crystallizer. After crystallization the mixture was filtered through a Buckner funnel under vacuum and the residue was washed with chilled hexane at 4° C. The crystals were dried, purity and yield were checked. (Table 5)

Example 2

100 g of the SODD was dried under vacuum and mixed with 1.5 times of the volume 98:2 methanolic sulphuric acid reagent and stirred vigorously for 4 Hrs. After the esterification excess of the methanol was distilled out under vacuum. To the mixture added 50 ml of brine solution at 80° C. and removed the lower layer. The mixture washed with 250 ml of hot distilled water until free from acid and salt. The esterified mixture was crystallized at 10° C. for 15 hrs in a crystallizer. After crystallization the mixture was filtered through a Buckner funnel under vacuum and the residue was washed with chilled hexane at 4° C. The crystals were dried, purity and yield were checked. (Table 5)

Example 3

500 g of the SODD was dried under vacuum and mixed with equal volume of 98:2 methanolic sulphuric acid reagents and stirred vigorously for 4 Hrs. After the esterification excess of the methanol was distilled out under vacuum. To the mixture added 500 ml of brine solution at 80° C. and removed the lower layer. The mixture washed with 250 ml of hot distilled water until free from acid and salt. The esterified mixture was crystallized at 10° C. for 15 hrs in a crystallizer. After crystallization the mixture was filtered through a Buckner funnel under vacuum and the residue was washed with chilled hexane at 4° C. The crystals were dried, purity and yield were checked. (Table 5)

Example 4

500 g of the SODD was dried under vacuum and mixed with equal volume of 98:2 methanolic sulphuric acid reagents and stirred vigorously for 2 Hrs. The excess methanol was distilled out under vacuum at 60-70° C., and added 250 ml of brine solution and washed at 70° C. The lower layer was removed and the mixture was washed with 125 ml of hot distilled water until free from acid and salt. The esterified mixture was crystallized at 15° C. for 5 hrs in a crystallizer. After crystallization the mixture was filtered through a Buckner funnel under vacuum. The crystal collected was washed with chilled hexane at 4° C. The crystals were dried, yield and purity were checked. (Table 5)

Example 5

1000 g of the SODD was dried under vacuum and mixed with equal volume of 98:2 methanolic sulphuric acid reagents and stirred vigorously for 2 Hrs. After the esterification excess of the methanol was distilled out under vacuum. To the mixture added 500 ml of brine solution at 80° C. and removed the lower layer. The mixture washed with 250 ml of hot distilled water until free from acid and salt. The esterified mixture was crystallized at 10° C. for 8 hrs in a crystallizer. After crystallization the mixture was filtered through a Buckner funnel under vacuum and the residue was washed with chilled hexane at 4° C. The crystals were dried, purity and yield were checked. (Table 5)

Pilot Plant Trials

Example 6

10 Kg of the SODD was Esterified with 98:2 methanolic sulphuric acid reagent and stirred vigorously for 4 Hrs. After the esterification excess of the methanol was distilled out. To the mixture added hot water at 80° C. and removed the lower layer. The esterified mixture was crystallized in a crystallization unit. Winterized the esterified mass to 10° C. and maintained at this temperature with periodic slow stirring for 15 hrs in a crystallizer. After crystallization the mixture was filtered using vacuum filtration system and the residue was washed with chilled hexane at 4° C. The crystals were dried and purity and yield were checked. (Table 6)

Example 7

In another 10 Kg batch after all the process were carried out as above and filtration was done in a continuous rotary vacuum filter. The sterols filtered were scrapped from the surface of the filter and washed the crystals with chilled hexane (4° C.) and purity and yield were checked. (Table 6)

The main advantages of the present invention are the following.

1. This process is effective for the isolation of free sterols from SODD without affecting the nature of the other useful compounds.
2. In this process free sterols separated in the beginning of the SODD fractionation, which facilitate further treatment of the SODD.
3. In other process like molecular distillation and supercritical fractionation, the fractions contain other impurities requiring further fractionation. But here sterols only are separated by crystallization.
4. By this process sterols obtained was pure and no need for further purification like solvent extraction, saponification, etc.
5. After crystallization of sterols the residue contains methyl esters, steryl esters, Squalene, Tocopherols and traces of unknown compounds. Separations of these useful compounds can be integrated to sterol process with minimum additional steps and facilities.
6. In this process MeOH: $H_2SO_4$ mixture was used as reagent for esterification and compared to other enzymatic, molecular distillation, supercritical process and this is simple and cost effective process.
7. After simple washing with hexane yields very pure sterol crystals and therefore no recrystallization is required and hence higher yield of sterols.
8. After estarification and water washing the excess methanol can be recovered by distillation and reused for esterification.

9. The hexane used for washing is also reusable.
10. The residue obtained after hexane wash is recycled to recover sterols present in the residue.
11. By this process maximum separation of the pure sterols facilitate the further separation of sterylesters, Tocopherols squalene etc.

TABLE 1

Composition of the SODD, SFODD, PODD, RBODD.

| Sl.No. | Sample | SODD % | SFODD % | PODD % | RBODD % |
|---|---|---|---|---|---|
| 1. | Moisture | 2.51 | 2.64 | 0.57 | 0.16 |
| 2. | FFA | 34.43 | 31.87 | 85.35 | 77.13 |
| 3. | Neutral lipids | 37.89 | 17.18 | 10.87 | 12.65 |
| 4. | Unsap matter | 25.26 | 39.25 | 3.12 | 9.33 |
| 5. | Total sterols | 9.46 | 6.10 | 0.06 | 0.72 |
| 6. | Free Sterols | 7.64 | 5.03 | — | — |
| 7. | Tocopherols | 7.88 | 2.96 | 0.03 | 0.01 |

SODD - Soybean Oil Deodoriser distillate,
SFODD - Sunflower Oil Deodoriser distillate
PODD - Palm Oil Deodoriser distillate,
RBODD - Rice Bran Oil Deodoriser distillate

TABLE 2

Total Sterol Content and its Composition of SODD, SFODD, PODD, RBODD by HPLC Method

| | Sterols % | | | | |
|---|---|---|---|---|---|
| Sample | β-Sitosterol | Campesterols | Stigmasterols | Unidentified Sterol | Total % |
| Soybean oil Distillate | 37.73 | 22.09 | 25.92 | 0.88 | 9.46 |
| Sunflower oil Distillate | 3.53 | 0.87 | 1.70 | — | 6.10 |
| Palm oil Distillate | 0.03 | 0.02 | 0.02 | — | 0.07 |
| Rice Bran Oil Distillate | 0.37 | 0.15 | 0.20 | — | 0.72 |

TABLE 3

Total tocopherol and tocotrienol contents and its composition of SODD, SFODD, PODD, and RBODD by HPLC method

| | Tocopherols (ppm) | | | | Tocotrienols (ppm) | | | | |
|---|---|---|---|---|---|---|---|---|---|
| Sample | α | β | γ | δ | α | β | γ | δ | Total % |
| Soybean oil Distillate | 6099 | 352 | 50786 | 21589 | — | — | — | — | 7.88 |
| Sunflower oil Distillate | 26856 | 640 | 1325 | 744 | — | — | — | — | 2.96 |
| Palm oil Distillate | 300 | 2 | 10 | — | 712 | 51 | 1622 | 350 | 0.30 |
| Rice Bran Oil Distillate | 10 | — | 90 | — | 5 | — | 260 | 25 | 0.05 |

SODD - Soybean Oil Deodoriser distillate,
SFODD - Sunflower Oil Deodoriser distillate
PODD - Palm Oil Deodoriser distillate,
RBODD - Rice Bran Oil Deodoriser distillate

TABLE 4

Composition and Purity of the Phytosterols isolated from the SBODD, SFODD by HPLC method

| Sample | Sterols % | | | | Purity % |
|---|---|---|---|---|---|
| | β-Sitosterol | Campesterol | Stigmasterol | Unidentified Sterol | |
| Mixture of the sterol isolated from SODD | 35.59 | 19.33 | 38.61 | 4.78 | 98.31 |
| Mixture of the sterol isolated from SFODD | 55.79 | 8.91 | 25.31 | 7.01 | 97.03 |

SODD - Soybean Oil Deodoriser distillate,
SFODD - Sunflower Oil Deodoriser distillate

TABLE 5

Yield of the Phytosterols from Soybean Oil deodorizer distillate.

| Sl. No | Wt. of SODD (g) | Sterols (g) | Yield (%) |
|---|---|---|---|
| 1. | 100 | 6.7 | 87.70 |
| 2. | 100 | 6.5 | 85.08 |
| 3. | 500 | 33.40 | 87.43 |
| 4. | 500 | 32.72 | 85.65 |
| 5. | 1000 | 65.5 | 85.73 |

TABLE 6

Yield of the Phytosterols from Soybean Oil deodorizer distillate of 10 Kg batch.

| Sl. No. | Wt. of SODD (Kg) | Sterols (Kg) | Yield (%) |
|---|---|---|---|
| 1. | 10 | 0.672 | 87.96 |
| 2. | 10 | 0.658 | 86.13 |

We claim:

1. A process for the preparation of high purity phytosterols from deodourizer distillate from vegetable oils which comprises mixing deodourizer distillate from vegetable oils with a methanolic solution of sulfuric acid in a ratio of 1:1 to 1:1.5 (v/v), stirring the above said reaction mixture, at a temperature of 50-85° C., for a period of 2-4 hrs, distilling of the excess of methanol from the above said reaction mixture under vacuum, adding brine solution to the above said reaction mixture to separate sulfuric acid and removing the lower layer to obtain the ester layer, washing the above said ester layer with hot water till all of the acid and salts are removed, followed by crystallization at a temperature in the range of 0-25° C. for a period of 110 hrs, filtering and washing the resultant crystals obtained with chilled n-hexane, at a temperature of 0-10° C. to obtain the desired high purity phytosterols.

2. A process as claimed in claim 1, wherein the vegetable oil used for obtaining deodourizer distillate is selected from the group consisting of soybean oil, sunflower oil, rice bran oil, palm kernel oil and coconut oil.

3. A process as claimed in claim 1, wherein the sulfuric acid in methanolic solution of sulfuric acid used is in the range of 1-10%.

4. A process as claimed in claim 1, wherein the crystallization of the sterols is facilitated by bound water retained after water washing or added externally.

5. A process as claimed in claim 1, wherein the excess water present in the ester layer is released by controlled heating and is removed by decantation or centrifugation.

6. A process as claimed in claim 1, wherein the yield of fatty acid methyl esters obtained is 60-70% of DOD with 95-99% purity.

7. A process as claimed in claim 1, wherein the yield of phytosterols obtained is in the range of 80-90% of free sterols available in DOD with 95-99% purity.

8. A process for the preparation of high purity phytosterols from deodourizer distillate from vegetable oils, substantially as herein described with reference to the examples accompanying this specification.

* * * * *

UNITED STATES PATENT AND TRADEMARK OFFICE
CERTIFICATE OF CORRECTION

PATENT NO.      : 7,632,530 B2
APPLICATION NO. : 11/373933
DATED           : December 15, 2009
INVENTOR(S)     : Arumughan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 934 days.

Signed and Sealed this

Second Day of November, 2010

David J. Kappos
*Director of the United States Patent and Trademark Office*